United States Patent [19]

Keen

[11] Patent Number: 4,948,915

[45] Date of Patent: Aug. 14, 1990

[54] CATALYTIC PROCESS FOR PRODUCTION OF ALKOXYLATED ESTERS

[75] Inventor: Brian T. Keen, Charleston, W. Va.

[73] Assignee: Union Carbide Chemicals and Plastics Company Inc., Danbury, Conn.

[21] Appl. No.: 887,916

[22] Filed: Jul. 22, 1986

[51] Int. Cl.$^5$ .................. C07C 69/708; C07C 67/347; C07C 67/31
[52] U.S. Cl. .................................... 560/187; 560/145; 560/180; 560/186
[58] Field of Search ............... 560/187, 186, 180, 145, 560/60

[56] References Cited

U.S. PATENT DOCUMENTS 2,658,070 11/1953 Schmidle et al. .................... 560/186

FOREIGN PATENT DOCUMENTS 986714 3/1965 United Kingdom .

*Primary Examiner*—Vivian Garner
*Attorney, Agent, or Firm*—Reynold J. Finnegan

[57] ABSTRACT

The reaction of a monohydroxyl or dihydroxyl alcohol with an alpha, beta-unsaturated ester in contact with a strongly basic anionic exchange resin in the hydroxyl or alkoxide form is unexpectedly and unpredictably enhanced by proper control of the water content in the reaction mixture and the temperature at which the reaction is carried out.

21 Claims, No Drawings

CATALYTIC PROCESS FOR PRODUCTION OF ALKOXYLATED ESTERS

The reaction of alpha, beta-unsaturated compounds with primary alcohols or diols in the presence of ion exchange resins has been known for many years. Thus it has been known that alpha, beta unsaturated aldehydes, esters, ketones and nitriles will react in the presence of an anionic or cationic exchange resin to form the addition product.

Japanese 51-30046, issued to Osaka Gas KK, is a typical reference, it shows the reaction of an aldehyde with an alcohol using a tertiary ammonium strong basic anionic exchange resin (—OH type) as catalyst. The reference discloses the reaction of the aldehyde with an alcohol in aqueous medium. Though conversion of the aldehyde was high, conversion to the desired condensation product was generally lower.

The reaction of ketones with alcohols is exemplified by British Patent Specification No. 986,714 and Canadian Pat. No. 725,216 (both claiming priority on U.S. patent application Ser. No. 188,517 filed on Apr. 18, 1962), issued to Shell. In these references the catalyst is a strongly basic anionic exchange resin in the hydroxide form.

The use of a strongly acid cation exchange resin in the hydrogen form is disclosed in U.S. Pat. No. 2,871,269, issued to N. B. Lorette, to react a ketone with an alcohol to form the addition compound. This reference differs from the others in that an acid cation exchange resin is used rather than a basic anion exchange resin. A similar disclosure by N. B. Lorette is found in J. Org. Chem., 23, 973 (1958).

The reaction of an ester with an alcohol is exemplified by U.S. Pat. No. 2,658,070, issued to C. J. Schmidle et al. The catalyst used is an anion exchange resin having quaternary ammonium alkoxide groups at a temperature range of 0° C. to 90° C. The reference contains no recognition of the importance of temperature, alcohol to ester mole ratio and water to the reaction.

U.S. Pat. No. 2,430,436, issued to J. B. Tindall, prepares 4-methyl 4-alkoxy-2-pentanones from mesityl oxide and an aliphatic alcohol at a reaction mixture pH of between about pH 4 and pH 9. The reference does not disclose the use of ion exchange resin catalysts.

THE INVENTION

This invention is directed to an improved process for the production of hydrocarbyl hydrocarbyloxyalkanoates by the reaction of a monohydroxyl or dihydroxyl alcohol with an alpha, beta-unsaturated ester in the presence of a strong basic anionic exchange resin in the hydroxyl or alkoxide form. The particular process herein described and claimed is an improvement over the processes heretofore disclosed and produces results that were completely unexpected and unpredictable. When carried out under the conditions herein described one obtains the desired products at a reaction rate that can be as much as four to five times greater than the reaction rates previously obtained; in addition, the catalyst life is unexpectedly and unpredictably considerably enhanced, conversions are exceptionally high and a minimum amount of by-products is obtained.

The reaction is represented by the general equation:

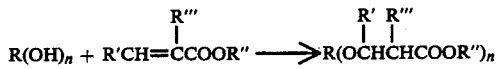

wherein R is a linear or branched monovalent alkyl group or a linear or branched divalent alkylene group or adivalent dialkylene ether or polyalkylene polyether group or a benzyl group; R' is hydrogen or an alkyl group; R" is an alkyl group or a phenyl group and R''' is hydrogen or methyl; all as hereinafter more fully defined; and n has a value of 1 or 2.

The monohydroxyl alcohols used as starting materials are represented by the general formula ROH, wherein R is a linear or branched alkyl group having from 1 to 8 carbon atoms, preferably from 1 to 3 carbon atoms, or a benzyl group that may or may not contain lower alkyl substituents in the ring portion thereof. Illustrative of suitable monohydroxyl alcohols are methanol, ethanol, propanol, isopropanol, butanol, sec-butanol, isobutanol, the pentanols, the hexanols, 2-ethylhexanol, benzyl alcohol, 4-methylbenzyl alcohol, and the like. It was observed that methanol causes transesterification of the ester.

The dihydroxyl alcohols used as starting materials are represented by the general formula $HO(RO)_mH$, wherein R is a divalent alkylene group having from 1 to 6 carbon atoms, preferably 2 to 3 carbon atoms and m is an integer having a value of from 1 to about 10, preferably 1 to 3. Illustrative of suitable dihydroxyl alcohols are ethylene glycol, diethylene glycol, triethylene glycol, 1,3-propylene glycol, 1,2-propylene glycol, dipropylene glycol, butylene glycols, pentylene glycols, hexylene glycols, and the like.

The alpha, beta-unsaturated esters used as starting materials are represented by the general formula:

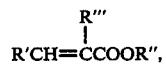

wherein R' is hydrogen or an alkyl group having from 1 to 3 carbon atoms, R" is an alkyl group having from 1 to 8 carbon atoms, preferably 2 to 5 carbon atoms and most preferably 2 or 3 carbon atoms, or a phenyl group and R''' is hydrogen or methyl. Illustrative of suitable esters are methyl acrylate, ethyl acrylate, propyl acrylate, butyl acrylate, 2-ethylhexyl acrylate, methyl crotonates, methyl 2-pentenoate, methyl 2-hexenoate, methyl methacrylate, ethyl mathacrylate, propyl methacrylate, and the like.

The reaction between the mono- or di-hydroxyl alcohol and the unsaturated ester requires one equivalent of unsaturated ester per hydroxyl equivalent. However, generally an excess of the hydroxyl compound is used to facilitate operation and handling and to assist in temperature control. The mole ratio of hydroxyl compound to ester can vary from about 3:1 to 100:1, preferably about 4:1 to 60:1 and most preferably about 8:1 to 30:1, with the proviso that at least equivalent reactive amounts of hydroxyl compound and unsaturated ester compound are used.

The catalysts used in the reaction are the strongly basic anionic exchange resins in either the hydroxyl form or alkoxide form or a combination of both forms. These compositions are well known to those of ordinary skill in the art and a large number are commercially available. These anionic exchange resins contain a polymer backbone having strongly basic functional groups incorporated into their structures. A preferred basic functional group is the quaternary ammonium base. The resins are generally used in the hydroxyl form; these, however, are convertible to the alkoxide form by passing the desired anhydrous alcohol through the resin. Illustrative of commercially available resins are the Amberlites*, Dowex*, Duolite* materials as well as many others known to those of ordinary skill in the art. Specifically one can mention Dow-MSA-1, DOWEX 1X-8, Rohm & Haas 904, Amberlite IRA-00, DOWEX 2, Duolite A-40, Duolite A-42, Nalcite* SAR.

The resins can be in the form of powders, beads or granules. They can be used in a fixed bed reaction system or in a dispersion or slurry reaction system. The amount of resin catalyst used will depend, of course, on the specific reactants employed, as well as the reaction conditions at which the process is conducted. In general, an amount of from about 0.1 weight percent or less to about 20 weight percent or more based on the ester present is employed when a slurry process is used and at the completion of the reaction the catalyst can be removed by conventional means, and recycled after regeneration if this is required.

The process is generally carried out using a fixed bed system, typically in a column or tank reactor. In a typical embodiment, the catalyst bed is generally prepared by flushing it with the dry selected alcohol to be used in the reaction; this alcohol can, if desired, contain other alcohols or a small amount of the unsaturated ester that will be used. The bed is then flushed with dry nitrogen, flushed with deionized water, again flushed with dry nitrogen followed by treatment with a 2–10 weight percent aqueous alkali metal caustic solution. The bed is then again washed with water, purged with nitrogen, flushed with fresh alcohol or the alcohol-ester mixture and purged with nitrogen. It is then washed with alcohol and purged with nitrogen, in sequence, until the water content in the alcohol outlet is preferably not greater than the water content in the alcohol feed. The wash components should preferably be anhydrous or almost so and they can be introduced to the bed at an elevated temperature if desired. The catalyst is then ready for use and is a highly active material that must be carefully handled to prevent spontaneous ignition. During continuous use the reaction rate will decrease and degeneration of the catalyst will be noticed; this is evidenced by incomplete reaction of the unsaturated ester with the hydroxyl compound, which is determined by analysis of the reaction product mixtures recovered for unreacted ester content. Normally, when unreacted ester breakthrough is about one weight percent, or higher (if desired up to several percentage points), the catalyst bed is regenerated following the procedure described. Bed preparation is not limited to the procedure described above since other sequences can be used with equally good results.

It was noted that the presence of water in the reaction mixture has a profound effect on the reaction, an observation that has not previously been reported in the published literature. That water content is important for the attainment of catalyst cycle life, high conversion rates and efficiencies has not been recognized by those skilled in the art. It was observed that maintenance of a water content of from about 0.01 to less than about 0.5 weight percent, based on the amount of ester and alcohol charged, leads to significant improvements; preferably the water content should be less than about 0.1 weight percent.

It was also noted that the mole ratio of alcohol to alpha, beta-unsaturated ester in the initial feed mixture plays an unexpected and unpredictable role in reaction rate, catalyst productivity and conversion time with higher mole ratios being more advantageous. Data supporting this is found in Example 24. This mole ratio can be from about 3:1 to about 100:1.

Catalyst deactivation can be indirect or direct. Indirect deactivation results from the presence of water in the system and is accelerated with increases in temperature. The presence of water in excess of about 0.1 weight percent should therefore be avoided.

Direct deactivation is caused by the presence of acids that will react with the basic groups in the catalyst molecule and render the catalyst inactive. Thus, traces of free acid in the system should be avoided. One manner in which acids may get into the system is hydrolysis of the unsaturated ester by the water present in the system. For this reason water content should be kept as low as possible. The water hydrolyzes the ester and forms acid that in turn neutralizes the catalyst by replacing the base on the catalyst and rendering the catalyst inactive. At higher temperatures this reaction sequence occurs more rapidly and greatly shortens the catalyst life, thus requiring more frequent reactivation. Thus, both water and acids are impurities to be avoided.

Though it is known that higher temperatures favor higher initial reaction rates and conversion rates, it was observed that the overall reaction rate and conversion may be lower at higher temperatures than at lower temperatures. Lower temperatures when combined with proper control of water content and alcohol to ester mole ratio in the feed result in unexpected and unpredictable reaction rates that can be as much as five times or more greater than can be achieved at higher temperatures as well as longer catalyst cycle life between reactivation. The temperature for the reaction can be from about −5° C. or lower to about 35° C., preferably from about 5° C. to about 30° C. and most preferably from about 10° C. to about 20° C. Even though lower temperatures are beneficial it has not heretofore been reported that reduction of the temperature below a certain point will preclude the reaction from taking place. Thus, at temperatures below about minus 5° C. we have observed that the reaction rate decreases significantly. At temperatures of about 50° C. and above the catalyst cycle life is commercially unacceptable.

The temperature of the reaction can be controlled by means known to the average skilled engineer. Thus, cooling means can be present in or around the catalyst bed, or the temperature can be controlled by feed rate and/or feed temperature. The reaction is an exothermic reaction and therefore it is preferable to have provision for temperature control. A convenient expedient for temperature control is to feed a pre cooled mixture of the hydroxyl compound and the unsaturated ester, say at a temperature below about 15° C., to the catalyst bed at such a rate that the temperature of the reaction mixture exiting from the catalyst bed is within the temperature range previously recited.

As is often the case with organic reactions and chemicals an inhibitor or stabilizer can be present in the feed, the final product, and in the reaction process steps. One or more inhibitor(s) can be present and mixtures are usually more effective. Conventional stabilizing amounts known to those skilled in organic chemistry are employed. Illustrative inhibitors include monoethylhydroquinone, phenothiazine, butylated-hydroxytoluene, hydroquinone, monomethyl ether of hydroquinone, etc.

The reaction is essentially a liquid phase homogeneous reaction even though the catalyst is a solid. The process can be carried out by passing a mixture of the liquid reactants through a bed of the catalyst or by stirring the mixture of reactants and catalysts. It can be a continuous, semi-continuous or batch process and the desired product is readily separated from the solid catalyst, which is then recycled, or regenerated and then recycled. Normally an excess of the alcohol is used, which serves as a diluent in the reaction. Since conversion of the ester to the hydrocarbyl hydrocarbyloxyalkanoate is essentially quantitative, separation of the desired product from the recovered reacted mixture is readily achieved by normal distillation procedures.

The reaction can be conducted at subatmospheric, atmospheric or superatmospheric pressure, with atmospheric pressure being the most convenient.

The reaction time is dependent upon the size of the batch, the particular reactants and catalyst used, and the temperature, as is known to those of ordinary skill in this art.

In a typical embodiment, an inhibitor-containing solution of the hydroxyl compound and unsaturated ester, at about a 15:1 mole ratio, is precooled to about 5° C. to 10° C. and passed through a bed of a strongly basic anionic exchange resin in the hydroxyl form that had been prepared and activated as described in this application. The solution was added at such a rate that the outlet temperature of the reacted mixture exiting from the catalyst bed was preferably from about 20° C. to about 25° C. Conversion of the unsaturated ester to the corresponding hydrocarbyl hydrocarbyloxyalkanoate was almost 100 percent. The alcoholic mixture was then distilled to recover the desired product.

As is recognized, one can use a mixture of alcohols and a single ester, or a single alcohol and a mixture of esters, or a mixture of alcohols and a mixture of esters. This is entirely dependent upon the ultimate product desired and mixtures of this nature are generally used only when mixed products are desired due to possible separation problems.

The hydrocarbyl hydrocarbyloxyalkanoates produced have the general formula:

$$R(OCHCHCOOR'')_n$$
$$\phantom{R(OCH}|\phantom{CH}|$$
$$\phantom{R(OCH}R'\phantom{CH}R'''$$

wherein R, R', R", R''' and n have the meanings heretofore defined. Illustrative of such compounds are those having the moities set forth below in which R''' can be either hydrogen or methyl:

| R | R' | R" | n |
|---|---|---|---|
| methyl | H | methyl | 1 |
| " | H | ethyl | 1 |
| " | H | n-propyl | 1 |
| " | H | i-propyl | 1 |
| " | H | n-butyl | 1 |
| " | H | 2-ethylhexyl | 1 |
| " | H | hydroxypropyl | 1 |
| " | methyl | methyl | 1 |
| " | ethyl | ethyl | 1 |
| " | propyl | ethyl | 1 |

-continued

| R | R' | R" | n |
|---|---|---|---|
| ethyl | H | methyl | 1 |
| " | H | ethyl | 1 |
| " | H | i-propyl | 1 |
| " | H | hexyl | 1 |
| " | methyl | ethyl | 1 |
| " | " | butyl | 1 |
| i-propyl | H | ethyl | 1 |
| " | methyl | " | 1 |
| n-butyl | H | " | 1 |
| hexyl | H | " | 1 |
| octyl | H | " | 1 |
| benzyl | H | " | 1 |
| methyl | H | phenyl | 1 |
| " | butyl | methyl | 1 |
| ethylene | H | methyl | 2 |
| " | H | ethyl | 2 |
| " | H | i-propyl | 2 |
| " | H | n-propyl | 2 |
| " | CH$_3$ | methyl | 2 |
| DEO | H | ethyl | 2 |
| " | H | propyl | 2 |
| " | CH$_3$ | ethyl | 2 |
| TEO | H | ethyl | 2 |
| 1,2-propylene | H | ethyl | 2 |
| " | CH$_3$ | ethyl | 2 |
| DPO | H | methyl | 2 |
| " | CH$_3$ | ethyl | 2 |
| " | H | ethyl | 2 | ethylene = —CH$_2$CH$_2$—
DEO = —CH$_2$CH$_2$OCH$_2$CH$_2$—
TEO = —CH$_2$CH$_2$OCH$_2$CH$_2$OCH$_2$CH$_2$—
1,2-propylene = 

DPO = —CHCH$_2$OCHCH$_2$—
　　　　　|　　　　|
　　　　CH$_3$　　CH$_3$

The products are esters that have excellent solvent properties and thus find use in the coatings industry and inks.

The following examples serve to describe different reactors and reaction systems employed and to further illustrate this invention.

A 2.54 cm (ID) by 76.2 cm long stainless steel tubular reactor (Reactor A) was charged with 150 ml of Dowex MSA-1* strongly basic anionic exchange resin. The reactor was equipped with a feed pump, thermocouples at the mid point and top of the catalyst bed and the necessary piping, gauges, pumps, valves and reservoirs to introduce reactants and recover products. The catalyst bed was treated, in sequence, with 900 ml of ethanol, 900 ml of water, 900 ml of 4 weight percent aqueous sodium hydroxide, 900 ml of water and 900 ml of ethanol to regenerate the bed before introducing the reactants feed containing anhydrous ethanol and ethyl acrylate. The ethyl acrylate contained 150 ppm phenothiazine as inhibitor.

Examples 1 to 17

A series of examples was conducted using Reactor A in which the concentration of the ethyl acrylate in the feed and the feed rate (expressed in LHSV Hr$^{-1}$) were varied to evaluate their effect on catalyst bed cycle life and temperature generated in the bed and the effect of the temperature on the bed cycle life. The catalyst bed cycle life is determined by ethyl acrylate breakthrough. When the amount of unreacted ester found in the product mixture exiting from the top of the reactor was about one weight percent or a preselected higher value this was a measure of the catalyst bed cycle life; the time in hours to reach this point is recorded as the bed cycle life. Due to the time and expenses required to regenerate the catalyst bed, for commercial practice a catalyst bed cycle life of less than about 50 hours is not economically acceptable. The results achieved were completely unexpected and unpredictable from the information publicly available. It was found that at average catalyst bed temperatures below about 35° C. catalyst bed cycle life values above about 50 hours for about a one weight percent ethyl acrylate breakthrough were achieved. (Examples 1 to 10) At average catalyst bed temperatures above about 35° C. catalyst bed cycle life values below 50 hours were achieved (Examples 11 to 17).

Table I summarizes the data for this series and the results achieved.

EA = ethyl acrylate

LHSV = liquid hourly space velocity; volume of liquid fed to the reactor per volume of catalyst per hour.

Breakthrough EA % Content = the EA content in the product stream at the reported Catalyst Bed Cycle Life.

acetic acid prior to regeneration as previously described. At 71 hours and an LHSV $Hr^{-1}$ of 2.0, the EA breakthrough was 2.4 weight percent.

Example 8: Prior to this run the regenerated bed was washed with a one percent solution of ethyl acrylate in ethanol. At 80 hours and an LHSV $Hr^{-1}$ of 0.9, the EA breakthrough was 3.4 weight percent.

Example 9: In this example the water content in the feed was between 0.05 and 0.1 weight percent and heated to 35° C. At 58 hours and an LHSV $Hr^{-1}$ of 1.7, the EA breakthrough was 0.84 weight percent. See comment to Example 17.

Example 10: The effect of increasing the catalyst bed temperature was investigated by heating the bed to 45° C. after the first 49 hours of reaction at the temperature indicated in the table. The catalyst was completely inactivated within 3 hours after the temperature was raised.

Example 11: The catalyst bed was not properly dried and contained 0.26 weight percent water, thus account-

| Ex. | EA in Feed Wt. % | Average LHSV Hr-1 | Inlet Feed Temp. °C. | Average Mid-point Temp. °C. | Average Top Temp. °C. | Catalyst Bed Cycle Life Hr | Breakthrough EA % Content |
|---|---|---|---|---|---|---|---|
| 1 | 15 | 2.1 | 9–13 | 26–27 | 25 | 100 | 0.5 |
| 2 | 15 | 2.0 | 19–20 | 26–30 | 28 | >105 | 0.3 |
| 3 | 15 | 2.0 | 13 | 28 | 26 | 90 | 0.8 |
| 4 | 10 | 2.0–2.7 | 21 | 29–30 | 28 | >98 | 0.4 |
| 5 | 15 | 2.0 | 17 | 26–29 | 26 | 80 | 0.5 |
| 6 | 19.6 | 1.0 | — | 26 | — | 76 | 0.9 |
| 7 | 10 | 2.0–2.7 | 21 | 28–29 | 26 | 50 | 0.5 |
| 8 | 15 | 1.5 | — | 34 | — | 64 | 1.1 |
| 9 | 10 | 2.7 | 35 | 35 | 32 | 56 | 2 |
| 10 | 19.6 | 1.0 | — | 33–34 | — | 50 | 0.3 |
| * | * | * | * | * | * | * | ** |
| 11 | 15 | 2.7 | 35 | 38–39 | 36 | 40 | 5 |
| 12 | 19.6 | 1.0 | — | 41 | — | 38–40 | 3.2 |
| 13 | 15 | 2.0 | 15 | 27 | 27 | 34 | 0.9 |
| 14 | 19.6 | 1.0 | — | 40 | — | 32 | 2.1 |
| 15 | 15 | 2.7 | 33 | 37–38 | 36 | 27 | 0.65 |
| 16 | 15 | 2.7 | 41 | 40–44 | 38 | 20 | 0.94 |
| 17 | 15 | 1.4 | 35 | 35 | 36 | 6.5 | 0.7 |

The following comments apply to the examples presented in Table I:

Example 1: The reaction was continued beyond 100 hours at an LHSV $Hr^{-1}$ of 2.0 until an EA breakthrough of 1.2% occurred between 117–119 hours total reaction time.

Example 2: Same as Example 1 at an LHSV $Hr^{-1}$ of 1.75; EA breakthrough of 1.9% observed at 117 hours total reaction time.

Example 3: The ester contained 10–20 ppm monmethylether of hydroquinone and 15 ppm of phenothiazine as inhibitor.

Example 4: In this example the feed contained 85 to 90 weight percent methanol and 10 to 15 weight percent ethyl acrylate. The catalyst bed was still active at 98 hours total reaction time at LHSV $Hr^{-1}$ of 4; at this time the EA breakthrough in the product stream was 0.4 weight percent and the methyl acrylate content was 1.5 weight percent.

Example 5: Example continued at an LHSV $Hr^{-1}$ of 1.7; after 95 hours the EA breakthrough observed was 2.4 weight percent and after 97 hours it was 3.1 weight percent.

Example 6: At 100 hours and an LHSV $Hr^{-1}$ of 0.65, the EA breakthrough was 4 weight percent.

Example 7: Before this run, the catalyst bed was treated with 6 bed volumes of one percent aqueous ing for the less than desired results achieved.

Example 12: In the reaction time period between 36 hours and 43 hours the EA breakthrough went from 0.15 to 7 weight percent.

Example 13: This run was shut down after 34 hours and left to stand at room temperature over the weekend and then resumed. After a total of 49 hours of feed the EA breakthrough was 10 weight percent.

Example 14: In the reaction time period between 23 and 36 hours the EA breakthrough went from 0.13 to 7 weight percent.

Example 15: In this run the feed was added at a temperature of 33° to 34° C.

Example 16: In this run the feed was added at a temperature of 41° C.

Example 17: In this example the water content in the feed was 0.45 weight percent. At 13 hours and an LHSV $Hr^{-1}$, the EA breakthrough was 10.5 weight percent. Comparison of this example with Example 9 shows the harmful effect of the higher moisture content in the feed stream.

The beneficial effect of precooling the feed is apparent; it leads to a longer catalyst bed cycle life. Also apparent is the deleterious effect of moisture. The ethyl 3-ethoxypropionate produced in Examples 1 to 17 was recovered by distillation.

Example 18

A reaction was carried out to study the effect of the presence of final product in the reaction feed. In this example Reactor A was used and the feed was a mixture of 61 weight percent ethanol, 15.9 weight percent ethyl acrylate and 23.1 weight percent ethyl 3-ethoxypropionate that was introduced to the reactor at an average LHSV $Hr^{-1}$ of 2. The moisture content in the feed was 0.04 weight percent. At intervals samples of the product stream were analyzed for ethyl acrylate (EA) and ethyl 3-ethoxypropionate (EEP) contents. The reaction was stopped at 40 hours due to the high ethyl acrylate breakthrough. The data and results are shown in Table II.

TABLE II

| Run Time Hr | Reactor Temp °C. Inlet | Mid-Point | Top | Product Stream Wt % EA | EEP |
|---|---|---|---|---|---|
| 1 | 9 | 30 | 26 | 0.17 | 45.9 |
| 2 | 8 | 30 | 28 | 0.18 | 45.9 |
| 18 | 8 | 26 | 27 | 0.24 | 45.9 |
| 24 | 8 | 26 | 29 | 0.46 | 45.5 |
| 28 | 8 | 26 | 27 | 1.06 | 44.8 |
| 40 | 6 | 20 | 25 | 9.88 | 31.8 |

After this 40 hours reaction period, the bed was regenerated and feed was resumed under the same conditions. The reaction feed was changed to 15 weight percent ethyl acrylate and 85 weight percent ethanol; after 50 hours the ethyl acrylate breakthrough was 0.08 weight percent, at 65 hours 0.15 weight percent, at 72 hours 0.18 weight percent, at 94 hours 0.38 weight percent, at 142 hours 2.9 weight percent and at 160 hours 6.7 weight percent. The feed was precooled and added at 7° C.

A second reactor was set up that would permit control of the temperature in the catalyst bed (Reactor B). This reactor was a 43 cm long stainless steel U-tube having an inside diameter of 0.9 cm, equipped with thermocouples and the necessary cooling tube to precool reactants mixture before entering the reactor containing the catalyst, piping, gauges, pump, valves and reservoirs to introduce reactants and recover products. The reactor and cooling tube were fully immersed in a cooling bath. The catalyst charged was 25 ml of Dowex MSA-1* strongly basic anionic exchange resin that was then purged with 250 ml of anhydrous ethanol to displace any moisture.

Examples 19-21

Reactor B was used to produce ethyl 3-ethoxypropionate from a feed containing 15 weight percent ethyl acrylate in ethanol; the moisture content was 0.05 weight percent. The effect of temperature was studied and it was observed that the catalyst bed cycle life decreased as the temperature at which the reaction was carried out increased. The data from these runs cannot be compared directly to the data from Examples 1 to 17 due to the significant differences in the reactor configuration; however, they can be compared to one another. Due to the small size of this reactor and the partical size of the catalyst, excessive channeling of the reactants past the bed as a result of the large surface to volume area occurs. Nevertheless, the data does show the effect of temperature on catalyst cycle life. The data and results are summarized in Table III at a feed rate of about 2 LHSV $Hr^{-1}$.

TABLE III

| Ex. | Cat Bed Temp. °C. | Ethyl Acrylate Breakthrough, Hrs. to 1 wt. % | to 3 wt. % | to 3.76 wt. % |
|---|---|---|---|---|
| 19 | 16 | 52 | 131 | 160 |
| 20 | 25 | 48 | 64 | — |
| 21 | 35 | 33 | 39 | — |

As seen, increasing the temperature shortens the catalyst life. In Example 19, one could expect to continue to use the reactor for an additional period of time, but the experiments were arbitrarily terminated after the indicated reaction time and EA breakthrough. Use of a more efficient (larger) reactor would have avoided the channeling problem and provided longer catalyst cycle life. The sensitivity of the catalyst cycle life to temperature is apparent.

EXAMPLE 22

The effect of higher moisture content in the reaction system was evaluated by repeating Example 19, but in this instance the water content of the feed was increased from 0.05 weight percent to 0.14 weight percent. The reaction was carried out at 16° C. catalyst bed temperature. The catalyst cycle life was drastically reduced as evidenced by ethyl acrylate breakthrough of 1 weight percent in 28 hours (compared to 52 hours in Example 19) and of 3 weight percent in 52 hours (compared to 131 hours in Example 19). The sensitivity of the catalyst cycle life to water is apparent.

EXAMPLE 23

A 50 cm long, 5 cm diameter water-jacketted reactor (Reactor C) was charged with 1 liter of Dowex MSA 1 strong base resin. The resin was treated in sequence with 2000 ml of ethanol, 2000 ml of water, 3800 ml of 4 weight percent aqueous sodium hydroxide, and 5000 ml of methanol-ethanol mixture. This reactor was used to react mixtures containing ethyl acrylate and both methanol and ethanol to produce mixtures of ethyl 3-methoxypropanoate, methyl 3-ethoxypropanoate, ethyl 3-ethoxypropanoate and methyl 3-methoxypropanoate. In each run about 7.5 liters of a feed solution containing the components identified in Table IV was used. There was no problem of ethyl acrylate breakthrough at the end of each run. The mixture was recovered by distillation to remove the alcohols.

TABLE IV

| Run | Feed, Wt. % EA | CH3OH | C2H5OH | Temp. °C. | Aver. LHSV Hr-1 |
|---|---|---|---|---|---|
| A | 20 | 20 | 60 | 24–26 | 2 |
| B | 20 | 23 | 57 | 24–26 | 2 |
| C | 20 | 37 | 43 | 24–26 | 2 |
| D | 20 | 10 | 70 | 24–26 | 2 |

EXAMPLE 24

Two hundred ml of Dowex SBR strongly anionic exchange resin in the hydroxide form was placed in a 500 ml covered addition funnel and washed by passing 500 ml of distilled water through the resin at a rate of 200 ml per hour. The resin was then flushed with dry ethanol at about the same rate until analysis of the effluent showed a water content of 0.1 weight percent; a total of 1,170 ml of dry ethanol was used. The wet resin was then placed in a sealed tube equipped with a gas inlet tube fitted with a porous filter at the end which extended to the bottom of the resin bed and a gas outlet tube. Dry nitrogen was passed through the inlet tube and the resin was purged overnight at room temperature to dry it.

A 250 ml, round bottom reactor flask was equiped with a water-cooled condenser, thermometer, inlet septum and magnetic stirrer. The reactor was immersed in a cooling bath and a 5 ml portion of the resin catalyst prepared above was added followed by the amounts of ethyl acrylate, ethanol and toluene indicated below. The reaction mixtures were then stirred and periodically sampled and analyzed to determine the effect of concentration of ethyl acrylate in the initial feed and temperature on conversion.

In Runs A and B, the reactor was charged with 49 g of ethyl acrylate, 49 g of ethanol and 2 g of toluene as an inert solvent. The mole ratio of alcohol to acrylate was 2.17:1. Run A was carried out at 25° C. and Run B at 41° C. Samples were removed and analyzed for weight percent unreacted ethyl acrylate at intervals as a measure of the rate of conversion of the ethyl acrylate to product, ethyl 2-ethoxypropionate. The results are shown below:

| Reaction Time, min. | Unreacted Ethyl Acrylate, Wt % | |
|---|---|---|
| | Run A (25° C.) | Run B (41° C.) |
| 80 | 20.8 | 11.9 |
| 160 | 9.5 | 6.5 |
| 240 | n.a. | 5.0 |
| 320 | 2.6 | 4.5 |
| 1290 | 0.3 | 3.9 |

As seen from the data, at the higher temperature there is an initially faster reaction and conversion rate. However, the catalyst is deactivated within a shorter period as evidenced by higher concentrations of unreacted ethyl acrylate in the reaction mixture after 320 minutes and essentially complete reaction at 25° C. (Run A) with only 0.3 weight percent unreacted ethyl acrylate after 1290 minutes whereas at 41° C. (Run B) there was still 3.9 weight percent unreacted ethyl acrylate or almost 8% of the original amount of ethyl acrylate added that was still unreacted.

In Runs C and D, the reactor was charged with 19.6 g of ethyl acrylate, 78.4 g of ethanol and 2 g of toluene. The mole ratio was 8.7:1. Run C was carried out at 21° C. and Run D was at 41° C. Samples were removed and analyzed as was done for Runs A and B. The results are shown below.

| Reaction Time, min. | Unreacted Ethyl Acrylate, Wt % | |
|---|---|---|
| | Run C (21° C.) | Run D (41° C.) |
| 80 | 10.0 | 3.2 |
| 160 | 5.4 | 0.7 |
| 240 | — | 0.3 |
| 250 | 2.5 | — |
| 320 | 1.5 | 0.2 |
| 1100 | — | 0.1 |
| 1320 | 0.1 | — |

As seen from the data, at the higher temperatures there is initially a faster reaction and conversion rate. However, at the higher ethanol to ethyl acrylate mole ratio of the feed employed here the catalyst is not deactivated and complete conversion of the ethyl acrylate occurs in a shorter period of time. Comparison of the data of Runs C and D with that of Runs A and B shows the advantages obtainable by the use of such higher mole ratios when combined with a higher temperature.

A fifth run, Run E, was carried out at intermediate mole ratio and temperature. In this instance the reactor was charged with 34 g of ethyl acrylate, 64 g of ethanol and 2 g of toluene. The mole ratio of alcohol to acrylate was 4.1:1 and the reaction was carried out at 31° C. The results are shown below:

| Reaction Time, min. | Unreacted Ethyl Acrylate, Wt % |
|---|---|
| 80 | 10.7 |
| 160 | 3.8 |
| 246 | 1.6 |
| 320 | 0.9 |
| 405 | 0.5 |

The data shows a relatively fast reaction rate and short conversion periods within a short time under these conditions.

An experiment was carried out to ascertain the effect of recycling the catalyst from Run E after drying but without regeneration. No reaction was observed, the catalyst had become completely deactivated.

EXAMPLE 25

Reactor A was used to produce methyl 2-methyl 3-methoxypropionate by feeding a mixture of 15 weight percent methyl methacrylate in methanol to the catalyst bed at an average LHSV $Hr^{-1}$ of 1.5. The inlet temperature was 60° C., average mid point temperature was 30° C. and the average top temperature was 27° C. The catalyst bed cycle life was 11 hours and the methyl methacrylate breakthrough was 3.8 weight percent. Use of methyl methacrylate requires a higher feed temperature due to its lower reactivity as compared to the acrylate.

What I claim is:

1. In a process for the production hydrocarbyl hydrocarbyloxyalkanoates of the formula:

wherein n has a value of 1 or 2; R is (i) a linear or branched monovalent alkyl group having from 1 to 8 carbon atoms (ii) a divalent alkylene or divalent dialkylene ether or divalent polyalkylene polyether group wherein the alkylene group has 1 to 6 carbon atoms or (iii) a benzyl group; R' is (i) hydrogen or (ii) alkyl having from 1 to 3 carbon atoms; R" is (i) a linear or branched alkyl group having from 1 to 8 carbon atoms or (ii) a phenyl group and R''' is hydrogen or methyl by the reaction of a monohydroxyl alcohol of the formula ROH or a dihydroxyl alcohol of the formula HO(-RO)$_m$H where m has a value of from 1 to about 10 with an alpha, beta-unsaturated ester of the formula

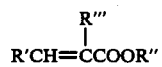

in contact with a strong basic anionic exchange resin catalyst in the hydroxide or alkoxide form, the improvement of enhancing the catalyst bed cycle life consisting of carrying out the reaction at a temperature of from about minus 5° C. to about 35° C., at a moisture content of from about 0.01 to about 0.5 weight percent and a mole ratio of alcohol to ester of from about 3:1 to about 100:1.

2. The improved process claimed in claim 1 wherein ROH is methanol.

3. The improved process claimed in claim 1 wherein ROH is ethanol.

4. The improved process claimed in claim 1 wherein ROH is a mixture of methanol and ethanol.

5. The improved process claimed in claim 1 wherein $HO(RO)_mH$ is ethylene glycol.

6. The improved process claimed in claim 1 wherein

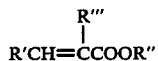

7. The improved process claimed in claim 1 wherein the mole ratio alcohol to ester is from about 4:1 to about 60:1.

8. The improved process claimed in claim 1 wherein the mole ratio of alcohol to ester is from about 8:1 to 30:1.

9. The improved process claimed in claim 1 wherein the temperature is from about 5° C. to about 30° C.

10. The improved process claimed in claim 9 wherein

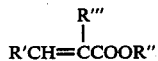

is ethyl acrylate.

11. The improved process claimed in claim 10 wherein ROH is methanol.

12. The improved process claimed in claim 9 wherein the moisture content is less than 0.1 weight percent.

13. The improved process claimed in claim 12 wherein the mole ratio of alcohol to ester is from about 8:1 to 30:1.

14. The improved process claimed in claim 1 wherein the temperature is from about 10° C. to about 20° C.

15. The improved process claimed in claim 14 wherein the moisture content is less than 0.1 weight percent.

16. The improved process claimed in claim 15 wherein

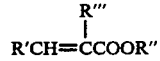

17. The improved process claimed in claim 15 wherein the mole ratio of alcohol to ester is from about 8:1 to 30:1.

18. The improved process claimed in claim 14 wherein

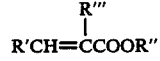

19. The improved process claimed in claim 18 wherein ROH is methanol.

20. The improved process claimed in claim 18 wherein ROH is ethanol.

21. The improved process claimed in claim 18 wherein ROH is a mixture of methanol and ethanol.

* * * * *

UNITED STATES PATENT AND TRADEMARK OFFICE
CERTIFICATE OF CORRECTION

PATENT NO. : 4,948,915

DATED : August 14, 1990

INVENTOR(S) : Brian T. Keen

It is certified that error appears in the above-identified patent and that said Letters Patent is hereby corrected as shown below:

Column 1, line 8, insert an hyphen between "beta and unsaturated".

Column 4, line 58, insert an hyphen between "pre and cooled".

Column 6, line 45 and Column 12, line 31, insert an hyphen between "mid and point".

Column 10, line 35, insert an hyphen between "MSA and 1".

Column 13, line 19 and Column 14, lines 19 and 28, after the formula insert the phrase -- is ethyl acrylate --.

Signed and Sealed this

Nineteenth Day of November, 1991

Attest:

HARRY F. MANBECK, JR.

*Attesting Officer*  *Commissioner of Patents and Trademarks*